United States Patent [19]
Mazess et al.

[11] Patent Number: 5,748,704
[45] Date of Patent: May 5, 1998

[54] PERIPHERAL BONE DENSITOMETER

[75] Inventors: Richard B. Mazess; Jens Borg, both of Madison; David L. Ergun, Verona, all of Wis.

[73] Assignee: Lunar Corporation, Madison, Wis.

[21] Appl. No.: 814,800

[22] Filed: Mar. 10, 1997

[51] Int. Cl.⁶ .................................................. G01B 15/02
[52] U.S. Cl. .......................... 378/54; 378/180; 378/192; 378/196
[58] Field of Search ........................ 378/54–56, 180, 378/196, 192

[56] References Cited

U.S. PATENT DOCUMENTS

| | | | |
|---|---|---|---|
| 4,507,799 | 3/1985 | Shimkus | 378/180 |
| 4,829,549 | 5/1989 | Vogel et al. | 378/55 |
| 5,150,394 | 9/1992 | Karellas | 378/62 |
| 5,465,284 | 11/1995 | Karellas | 378/62 |

OTHER PUBLICATIONS

Brochure, Dual Energy X–Ray Bone Densitometer. Admitted prior art.

*Primary Examiner*—Craig E. Church
*Attorney, Agent, or Firm*—Quarles & Brady

[57] ABSTRACT

A compact peripheral densitometer allows multi-use imaging of the foot and arm by means by simple rotation of the entire unit to be supported on different portions of its base at either of two angles. A slot in the unit may thus open upward for foot imaging when the unit is placed on the ground or open sideways for arm imaging with the unit resting on a table or the like.

9 Claims, 4 Drawing Sheets

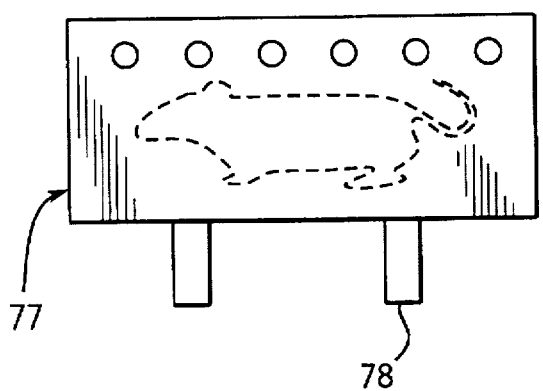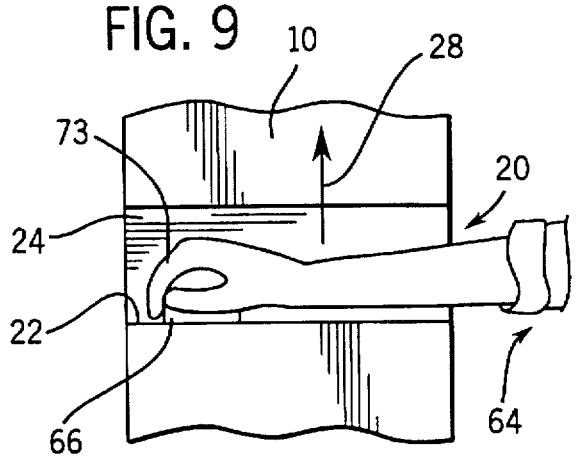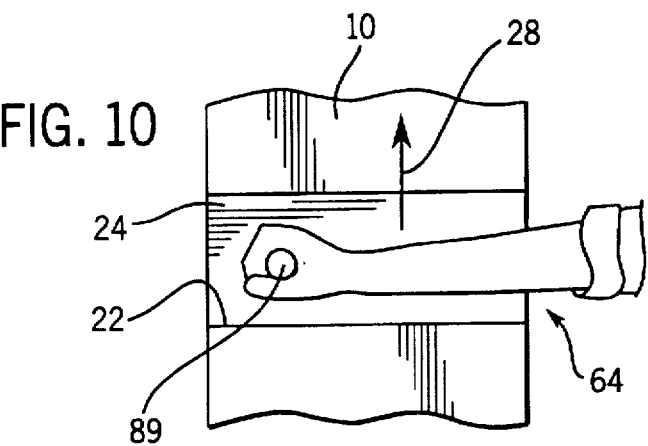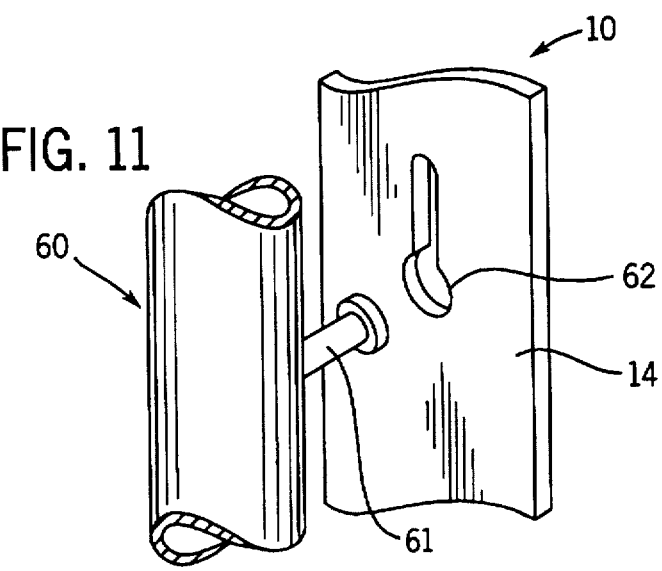

5,748,704

PERIPHERAL BONE DENSITOMETER

BACKGROUND OF THE INVENTION

The invention relates to bone densitometers such as are useful in the study of osteoporosis and in particular to a compact, multi-purpose bone densitometer providing multiple imaging orientations.

Bone densitometry equipment attempts to characterize the health status of bone as indicated by bone density or other structural aspects of the bone. Typically such densitometers employ a form of penetrating radiation directed through a bone of interest and its surrounding soft tissue and detected after passing through the bone by a radiation detector. The radiation source may be ionizing radiation from a radioisotope or x-ray tube. Example, x-ray and radioisotope bone densitometers are described in U.S. Pat. Nos.: 5,228,068; 5,253,282; 5,291,537; 5,305,368; 5,306,306; and 5,509,042 assigned to the present assignee and hereby incorporated by reference.

Measurements commonly made with radioisotope or x-ray densitometers include bone mineral density (BMD), based on either area or volume, total bone mineral content (BMC), or morphometric measurements indicating changes to the bone shape or its internal structure.

Of particular interest in the study of osteoporosis is the measurement of bone in the axial skeleton principally the spine and femur. Loss of bone material in the axial skeleton can cause a collapsing or crushing of individual vertebrae or a debilitating fracture of the femur or hip. Like other bones in the body, the axial bone includes an outer cortical layer providing an essentially continuous shell and an inner trabecular layer composed of a matrix of strut-like members. The trabeculae essentially cross-brace the bone to provide lightness and rigidity. A relatively minor loss of bone in the trabeculae can have a significant effect on bone strength, and hence it is desirable that a bone densitometer be sensitive to minor changes in trabecular bone.

Unfortunately the axial skeleton is surrounded by considerable amounts of soft tissue and therefore sophisticated and relatively expensive equipment must be used for accurate bone density measurement of the axial skeleton. It has been shown, however, that other bones in the body that are more accessible than those of the axial skeleton may reflect the condition of the axial skeleton. In particular, bones of the heel (the os calcis) and of the forearm, (the radius/ulna) are of interest. The os calcis includes a high proportion of trabecular bone and is known to be very metabolically active. The radius/ulna or forearm provides a different mix of cortical and trabecular bone.

Both of these bones are relatively free from surrounding soft tissue, so simpler machines, commonly referred to as peripheral densitometers, have been constructed to make bone density readings on these bones. Some of these machines are able to make measurements of both the os calcis and the forearm. Such dual purpose peripheral densitometers have been single energy systems which require that the forearm or heel be submerged in a water bath. Because of this, such dual purpose peripheral densitometers have been dedicated to measuring only one site, i.e., the heel or the forearm.

There is a need for a commercially practical compact peripheral densitometer that would permit densitometric measurements of both the os calcis or the radius/ulna.

BRIEF SUMMARY OF THE INVENTION

The present invention provides a mechanically simple, multi-purpose compact peripheral densitometer that may be used for imaging and measurement of both the bones of the heel or forearm.

Generally a dual energy beam is used to eliminate the effects of variations in soft tissue normally addressed in machines of this type through the use of a water bath. Eliminating the water bath permits flexible use of positioners for multiple imaging uses including the heel, forearm and laboratory animals. Removing the water bath also allows the entire unit to be rotated for more comfortable patient positioning.

Specifically, the invention provides a compact peripheral x-ray densitometer for in vivo bone having a housing including a first positioner to receive and position a human heel with respect to the housing and a second positioner to receive and position a human forearm with respect to the housing. A dual energy radiation source directs radiant energy through bone as received by a positioner and a detector located to receive the radiant energy after passage through the bone provides an electrical signal dependent on the received radiant energy for each of two energies. Image processing circuitry provides a measure of the bone substantially independent of any surrounding soft tissue.

Thus it is one object of the invention to provide a versatile peripheral densitometer accepting a variety of positioners for different peripheral imaging tasks. By eliminating the equalizing water bath, interference with the positioners is reduced.

The housing of the compact peripheral x-ray densitometer may also include a first base portion to support the housing at a first orientation and a second base portion to support the housing at a second orientation whereby the housing may be rotated to, supported at, either the first or second orientation changing the direction of the x-ray axis.

Thus it is another object of the invention to provide a simple yet robust design for a multipurpose densitometer. The entire housing may be simply rotated to either the first or second orientation to be supported on either base portion to easily change the direction of the x-ray axis for imaging the heel or arm.

The radiation source may be x-rays and the detector may be a solid state x-ray detector.

It is yet another object of the invention to provide a high resolution imaging densitometer that may acquire an image, perform bone mineral density-type measurements and structure measurements that indicate the strength of trabecular portions of the bone. The x-ray beam provides detail that may be used to locate the measurement area and to characterize structures such as trabeculae.

The compact peripheral densitometer may include a third positioner to provide a restraint for a small laboratory animal.

Thus it is another object of the invention to provide a multi-purpose densitometer useful both for screening and for clinical investigation of small animals.

The foregoing and other objects and advantages of the invention will appear from the following description. In this description, reference is made to the accompanying drawings which form a part hereof and in which there is shown by way of illustration a preferred embodiment of the invention. Such embodiment does not necessarily represent the full scope of the invention, however, and reference must be made therefore to the claims for interpreting the scope of the invention.

BRIEF DESCRIPTION OF THE SEVERAL VIEWS OF THE DRAWINGS

FIG. 4 is a perspective view of the use of the compact peripheral densitometer of FIG. 1 in the vertical orientation for forearm scanning as attached to a vertical surface of a cart or the like;

FIG. 8 is a view of a small animal cage that may also be used with the present invention;

FIG. 9 is a elevational view of the compact peripheral densitometer of FIG. 4 in vertical orientation showing positioning of a patient's wrist on the wrist guide of FIG. 6;

FIG. 10 is a view similar to FIG. 9 showing positioning of a patient's forearm when the patient grasps the handgrip of FIG. 6; and FIG. 11 is a detail fragmentary rear elevational view of the densitometer in the orientation of FIG. 4 showing the sockets used to attach the densitometer to a vertical side of a cart or the like.

DETAILED DESCRIPTION OF THE INVENTION

Figure 1:
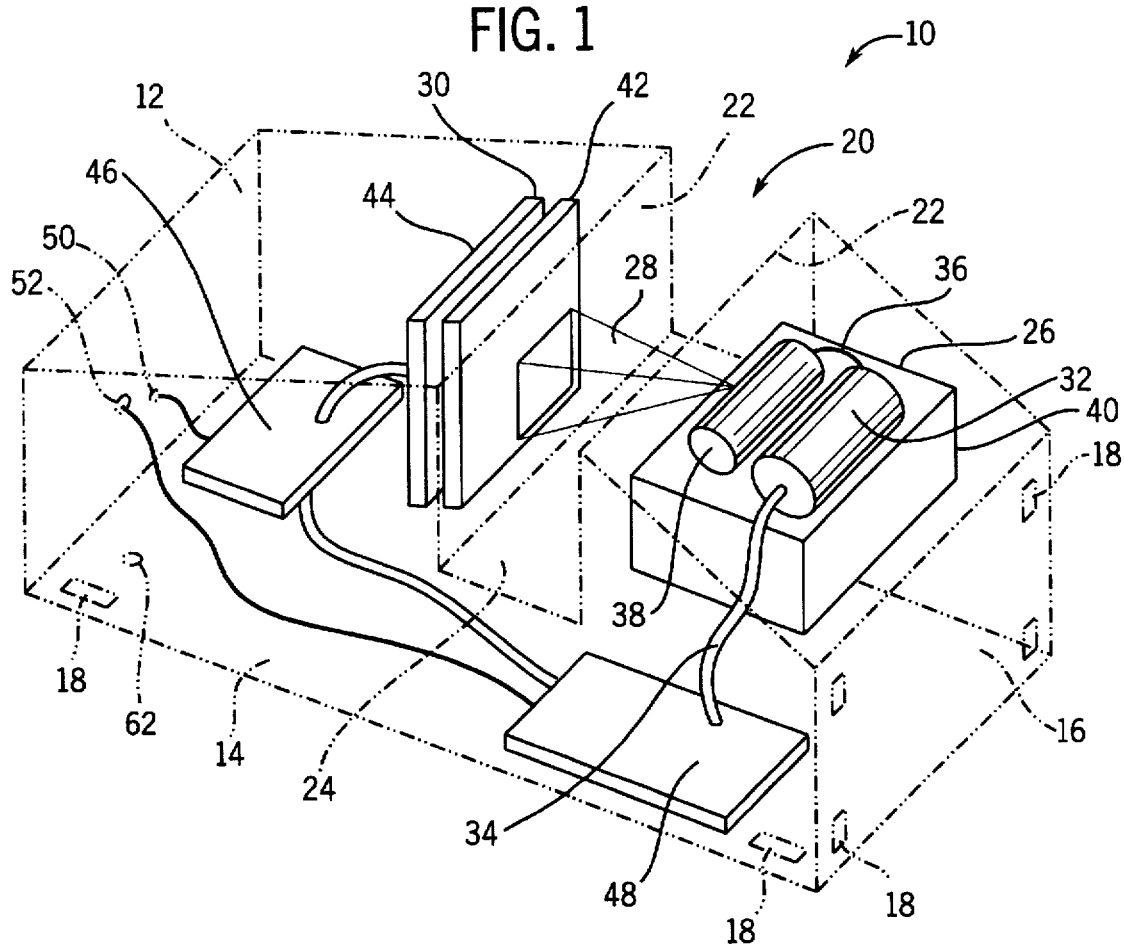
FIG. 1 is a perspective view in phantom of the compact peripheral densitometer of the present invention showing placement of an integral x-ray tube and power supply to project a collimated beam of x-rays across an access slot to a solid state detector.

Referring to FIG. 1, a compact peripheral densitometer 10 of the present invention includes a housing 12 having a generally rectangular primary base 14 on which it may rest. Abutting the primary base 14 at one end is an upstanding secondary base 16 perpendicular to base 14 and also generally rectangular.

Each of the bases 14 and 16 include elastomeric feet 18 providing a cushioning between the base 14 or 16 when the housing is rotated to rest on base 14 or 16, with base 14 or 16, in turn, resting on a horizontal support surface such as the floor or a table.

A slot 20 extends inward to the housing 12 toward primary base 14 in a face of the housing 12 opposite the primary base 14. The slot 20 has walls 22 generally parallel to secondary base 16 and a bottom 24 generally parallel to primary base 14.

Within the housing 12 on one side of the slot 20 is an x-ray source 26 projecting a collimated x-ray beam 28 through one wall 22 of the slot 20 and across the slot 20. The x-ray beam 28 then proceeds through a second wall of the slot 20 to be received by a solid state x-ray detector 30 positioned within the housing 12 on the other side of the slot 20 from the x-ray beam. The x-ray source 26 and detector 30 are fixed with respect to the housing 12.

The x-ray source 26 may be a 'monoblock' configuration in which a high voltage x-ray power supply 32 and an x-ray tube 38 are contained in a single rigid and transparent plastic block 40. The block 40 has cavities bored within it to receive the tube 38 and power supply 32 and interconnecting high tension lead 36. A clear silica potting compound is placed within the remaining portions of the cavity between the block 40, x-ray tube 38 and power supply 32. The potting compound remains in a gel-like state to permit expansion of these components with heating and operation, but to otherwise hold the components securely in an insulated fashion and to protect them from shock.

The clear block 40 permits inspection of the internal components for electrical arcing and allows embedded instrumentation, such as for temperature and the like, to be placed proximate to the components of the x-ray tube 38 and power supply 32 yet viewed after assembly. The monoblock design simplifies calibration and replacement of the x-ray source and provides a short and fully enclosed high tension lead 36.

The x-ray power supply 32 receives low voltage through power supply leads 34 from a power supply board 48 and converts it to one of two high voltage levels near a nominal voltage of 90 kilovolts with 0.9 milli-amps of current.

According to a command from a controller board 46 to be described. The power supply board 48 receives power through an external connector 52 which may be connected via a conventional cord to a source of line voltage.

The x-ray detector 30 receiving the x-ray beam 28 from the x-ray source 26 is square and has an area of 100 mm by 100 mm providing an 80 mm by 80 mm imaging area within the slot 20 suitable for measuring both the os calcis and the radius/ulna as will be described. The x-ray detector 30 includes a scintillation plate 42 converting x-ray photons to light. The scintillation plate 42 is followed by a charge coupled image detector (CCD) 44 such as is understood in the art. The CCD detector 44 includes 512 elements by 512 elements so as to provide resolution on the order of 0.1 mm. This high resolution permits not only imaging but structural analysis of the imaged bone including morphometry and measurement of the trabeculae. The image may be used to localize other measurement or to identify a single location in multiple studies over time.

An x-ray filter such as lead glass (not shown) may be placed between the CCD 44 and the scintillation plate 42 to stop x-rays passed by the scintillation plate 42.

The present invention uses dual energy imaging. Dual energy refers to radiation at two or more bands of energy, emitted simultaneously or in rapid succession, or a single broad band energy of more than a few kev over the diagnostic imaging range. Dual energy techniques allow the decomposition of an arbitrary material into two basis materials as described in detail in the article "Generalized Image Combinations in Dual KVP Digital Radiography", by Lehmann et al. Med. Phys. 8(5), Sept/Oct 1981. In the present invention, the dual energy is used to selectively image the bone without regard to variations in soft tissue and thus to permit elimination of an equalizing water bath.

Dual energy measurements may be provided either by affecting the source, e.g., removing or adding an x-ray filter, or by controlling the switching of energies to the source, i.e., switching between high and low x-ray tube voltage. Alternatively, dual energy measurements may be provided by using a conventional single or broad band energy x-ray but modifying the detector (e.g., detecting multiple energy thresholds or using multiple energy discriminating detectors that are selectively sensitive to one energy band.

In the present invention, a controller board 46 receives electrical signals from the CCD 44 and provides signals to a power supply board 48 to switch the voltage of the power supply 32 to the x-ray tube providing alternating and pulsed dual energy x-ray beams for the purpose of dual energy measurements. The controller board 46 provides the image data from the CCD 44 to an external connector 50 such as may be connected via cable (not shown) to a remote computer for data processing. It will be understood, however, that the processing capability may also be contained on the controller board 46 and a self-contained display on the housing may be used.

The preferred embodiment of the compact peripheral densitometer describes using an x-ray beam collimated into a cone beam and detected by an area detector. The area detector could be a small image intensifier, a scintillator and CCD arrangement, or a solid state semiconductor detector such as an amorphous silicon detector. The area detector provides the advantage of speed and high resolution. A disadvantage is that area detectors are more susceptible to scattered radiation.

Alternative embodiments could be pencil beam x-ray systems which use a raster scanning procedure or small fan beam with a linear or multilinear array detector. These later alternatives have the disadvantage of being slower to acquire an image and would require a more complicated scanning mechanism. While not preferred, such systems should be considered to come within the scope of the claims.

Figure 2:
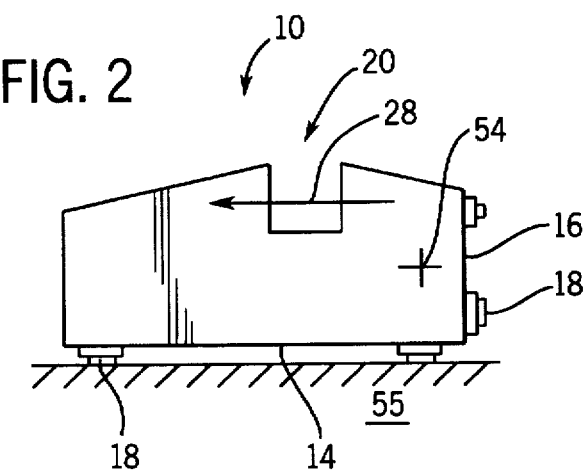
FIG. 2 is a front elevational view of the compact peripheral densitometer of FIG. 1 in a horizontal orientation resting on a floor as is suitable for use in foot scanning.

Referring now to FIG. 2, the placement of the x-ray source 26 and in particular the x-ray power supply 32 is toward base 16 so that a center of mass 54 of the compact peripheral densitometer 10 is displaced toward base 16. When base 14 is resting atop a support surface 55, the slot 20 opens generally upward and the x-ray beam 28 is directed horizontally across the slot 20. In this case, the center of mass 54 is off center above base 14. However, base 14 is large and the center of mass is low so the unit is stable despite the off center of mass. As will be described, this orientation is suitable for convenient imaging of the os calcis of the foot when the compact peripheral densitometer 10 is placed against the floor as surface 55.

Figure 3:
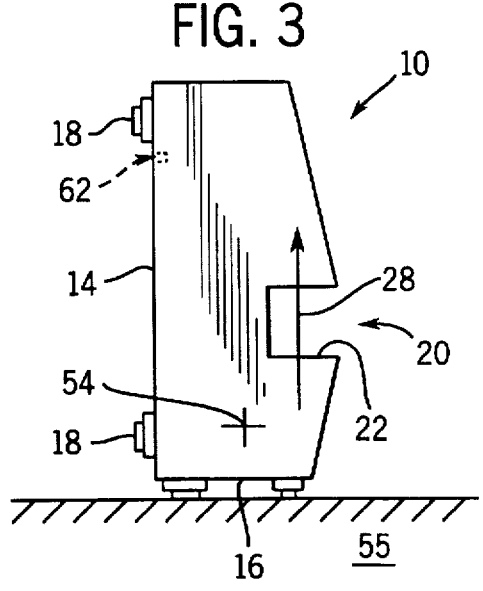
FIG. 3 is a figure similar to that of FIG. 2 showing the compact peripheral densitometer in a vertical orientation resting on a table surface or the like as is suitable for forearm scanning.

Referring to FIG. 3, alternatively, the compact peripheral densitometer 10 may be rotated to rest against base 16 with base 14 extending upward from the support surface 55. The center of mass 54 is low and approximately centered above the base 16 providing for stability despite the smaller size of base 16. In this orientation, the slot 20 opens to the side and the x-ray beam 28 is directed vertically upward. Thus a simple rotation of the compact peripheral densitometer 10 allows a second orientation of the x-ray beam which is suitable for use in imaging the radius/ulna of the forearm.

Figure 4:
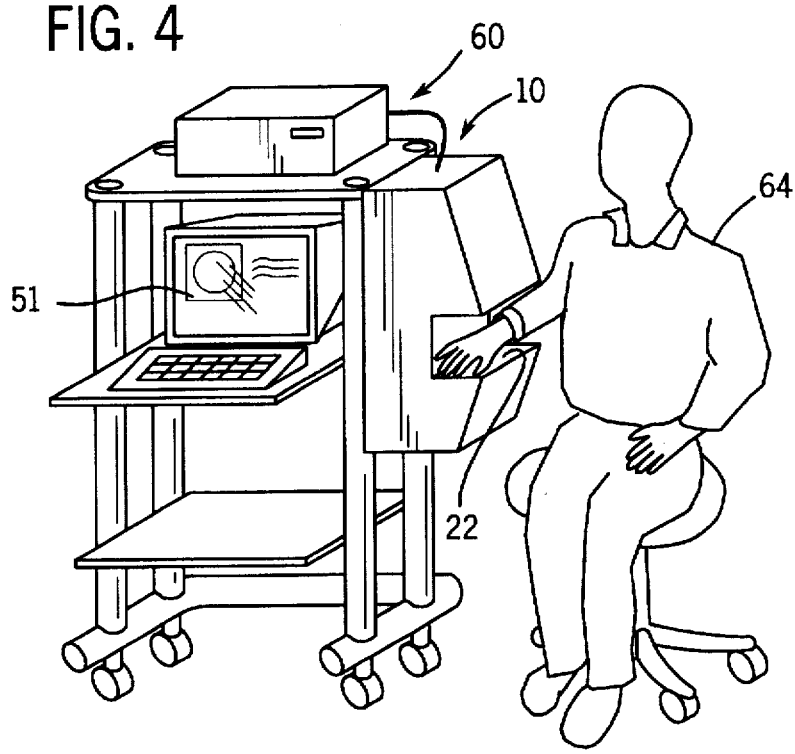

Referring now to FIGS. 4 and 11, alternatively, the vertical orientation may be obtained by hanging the compact peripheral densitometer 10 on a vertical wall or the side of a cart 60 which may have outwardly extending pegs 61 to be received within keyhole shaped sockets 62 in the base 14. The cart 60 may hold a desktop computer 51 connected to the controller board 46 (FIG. 1) and providing processing of dual energy image data according to techniques well known in the art.

Referring still to FIGS. 3 and 4 in the application of the compact peripheral densitometer 10 for imaging the bones of the arm, a patient 64 may be seated next to the compact peripheral densitometer 10 and the patient's arm inserted within the slot 20, palm down against a now lower wall 22 of the slot 20. The compact peripheral densitometer 10 is elevated by mounting on the cart 60 or placement on a desk or console so that the slot 20 is at a comfortable distance above the patient's waist.

Figure 6:
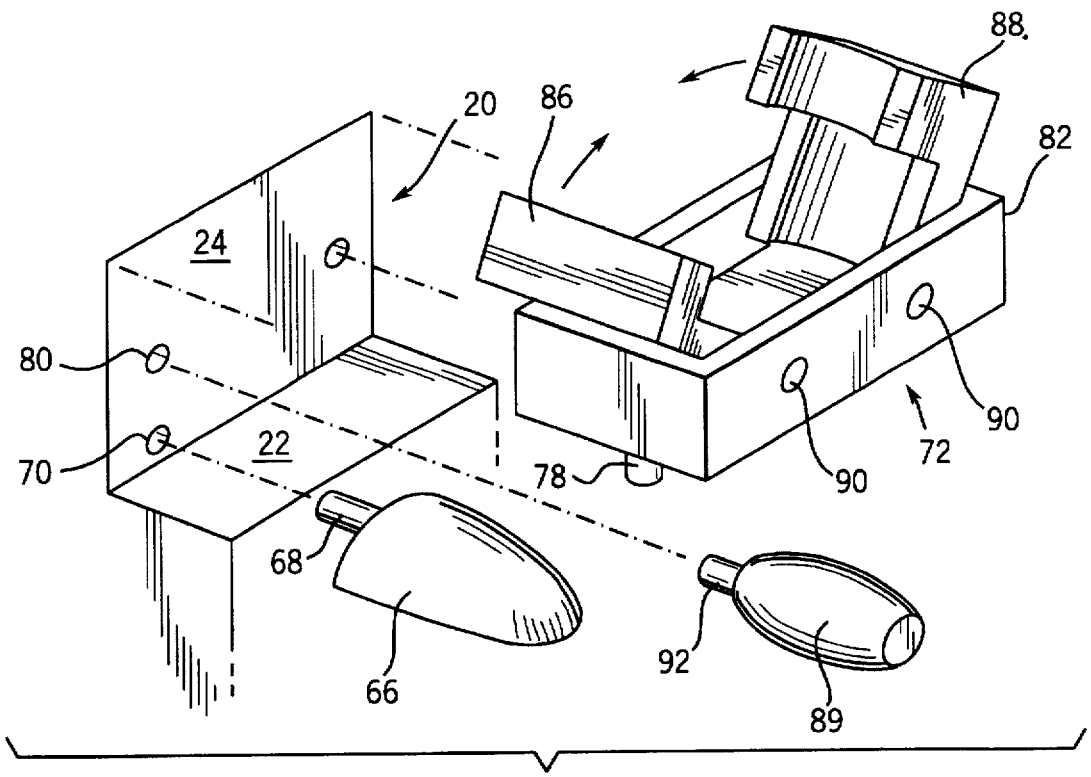
FIG. 6 is an exploded fragmentary view of the access slot with the compact peripheral densitometer positioned in the vertical orientation of FIG. 3 showing placement of a palm rest or handgrip for forearm imaging and placement of a heel positioner for foot imaging.

Referring now to FIGS. 6 and 9, in order to further facilitate the placement of the patient's arm within the compact peripheral densitometer 10, a palm rest 66 may be inserted against now lower wall 22 to rest on. The top surface of the palm rest 66 approximates that of a tapered half cylinder with a rounded end to conveniently fit within a patient's palm with the patient's fingers 73 curled over the rest 66 and the heel of the patient's palm positioned against a point at which the palm rest 66 rises from the wall 22. Palm rest 66 is removably mounted in the slot 20 by means of a guide peg 68 fitting within a bore 70 cut in the bottom 24 of the slot 20. When the guide peg 68 is fit within the bore 70, a lower flat surface of the palm rest 66 lies flush against wall 22.

With the patient's hand so positioned on the palm rest 66, x-rays pass vertically through the radius/ulna of the forearm to provide a reading of the density of the bone in that region.

Alternatively, referring to FIGS. 6 and 10, a handgrip 89 sized to be grasped by the patient 64 against the palm of the hand with fingers and thumb on either side of the handgrip may be used to position the patient's forearm within slot 20. The handgrip has an axial guide peg 92 that may be inserted into a bore 80 in bottom 24 so that the handgrip 89 extends upward from the bottom 24.

Figure 5:
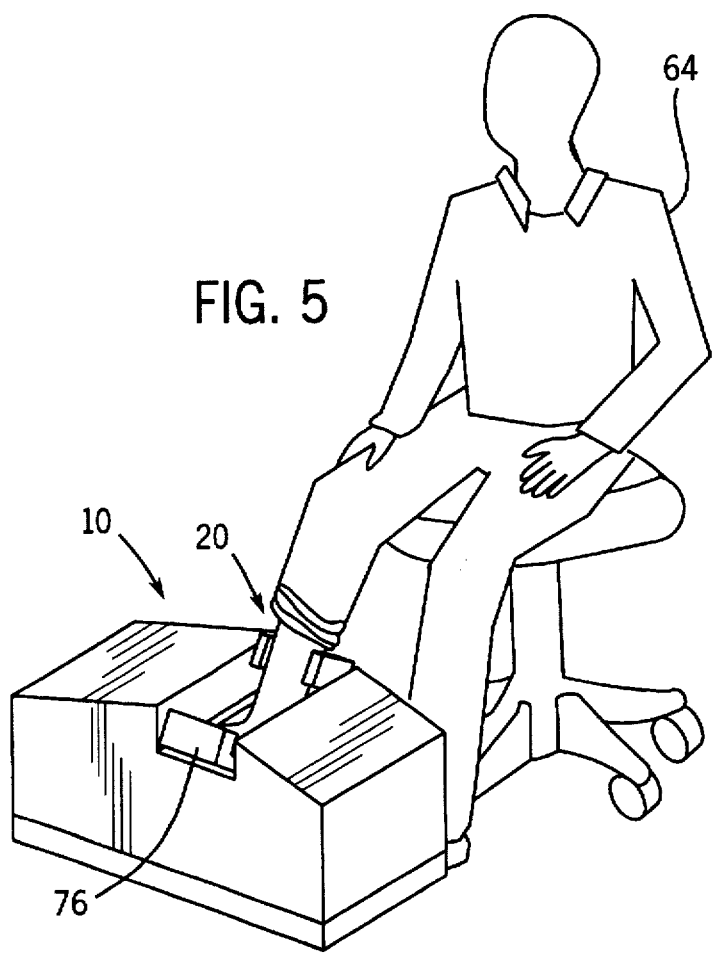
FIG. 5 is a view of the compact peripheral densitometer in the horizontal orientation of FIG. 2 showing positioning of a patient's foot within the access slot.

Referring now to FIGS. 2 and 5 in the application of the compact peripheral densitometer 10 for imaging the bones of the foot, the compact peripheral densitometer 10 may be placed on the floor with the patient 64 seated above it and the patient's foot placed in the upwardly open slot 20 in heel positioner 72.

Referring now to FIG. 6, the heel positioner 72 includes two downwardly extending guide pegs 78 received by corresponding bores 80 in the bottom 24 of the slot 20. The heel positioner 72 comprises a generally rectangular tray 82 opening upward and sized to fit within the slot 20 and to receive the heel of the patient when the tray bottom abuts the bottom 24 of the slot 20. Positioned at the ends of the tray 82, normally adjacent to the open ends of the slot 20, are a pivoting sole guide 86 and a pivoting calf guide 88. Sole guide 86 and calf guide 88 each extend upward from the bottom of the tray 82 at a relative angle of approximately 45 degrees to include a 90 degree angle to support the bottom of the foot and the back of the calf when the patient's foot is within the tray 82.

The bottom of the sole guide 86 and calf guide 88 toward the tray 82 is attached to the tray 82 by means of pivot pins 90 extending through the upward extending walls of the tray 82, through the lower extent of the sole guide 86 and calf guide 88, providing an axle for pivoting thereabout parallel to the bottom of the tray 82.

Figure 7:
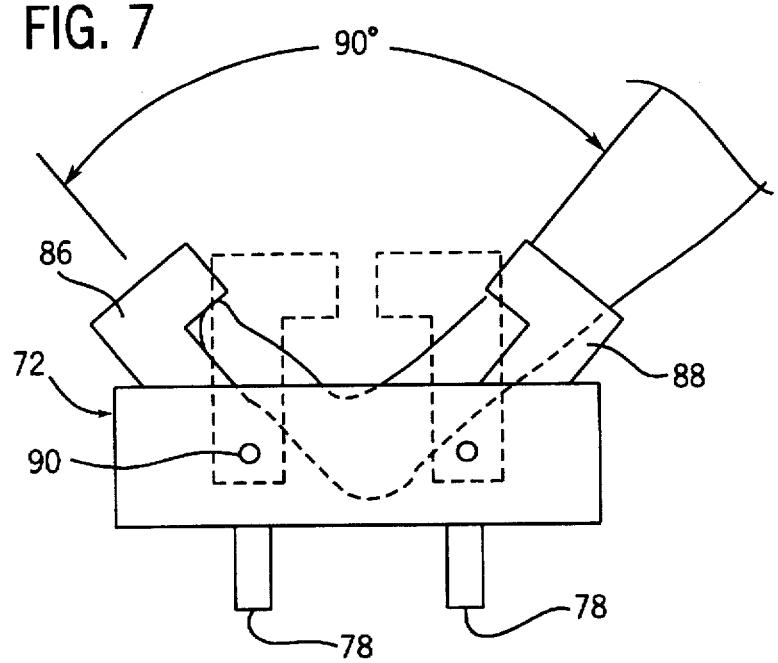
FIG. 7 is a front elevational view of the heel positioner of FIG. 6 having a patient's foot inserted therein and as folded indicated by phantom lines.

Referring now to FIGS. 6 and 7, when pivoted in a fully open position, the sole guide 86 and calf guide 88 are separated by nearly 90 degrees corresponding generally to the relaxed angle between the sole of the foot and the calf of the patient 64. As shown in phantom lines, however, by pivoting the sole guide 86 and calf guide 88 toward each other, they may be folded into a more compact configuration for storage or travel.

Referring generally again to FIGS. 1 and 4 during operation, the image data from the CCD 44 acquired for the dual x-ray energies may be processed by computer 51 and to reduce scatter by scatter estimation techniques, and to extract any attenuation caused by soft tissue so as to provide a measure of areal bone density uninfluenced by soft tissue thickness. As a result, the patient also need not remove socks or stockings for the measurement to be made.

Further, the use of dual energy measurements eliminates the needs for equalizing material such as a water bath or the like that compensate for varying soft tissue thickness. Consequently, the dual energy facilitates the simple rotation of the machine for different imaging purposes, such rotation that would be difficult if a water bath were required. By eliminating the influence of soft tissue, more complex densitometric methods such as a CT need not be used, thus radically simplifying the device.

In either orientation, an image of the bone within slot 20 may also be produced and the image used to identify a particular location of the os calcis or radius/ulna for the purpose of repeat measurements of that location over time for the particular patient. In addition, the imaging capability allows the trabeculae of the bone to be directly analyzed to provide yet another dimension to the evaluation of the measured bone.

Referring to FIG. 8, the compact size of the present invention also permits it to be used in other bone density applications including laboratory application in the measurement of bone mass of small laboratory animals. In this case, the positioners of palm rest 66 and heel positioner 72 as previously described may be removed and a radiotranslucent cage 77 having means for restraining the animals may be placed within the slot 20 for comparable measurements.

The above description has been that of a preferred embodiment of present invention. It will occur to those that practice the art that many modifications may be made without departing from the spirit and scope of the invention. For example, a pencil or fan beam of radiation may be used and scanned across the slot of the housing. Similarly, the detector may be a single or linear detector element conforming to the beam. Other types of detectors may be used other than CCD detectors. In order to apprise the public of the various embodiments that may fall within the scope of the invention, the following claims are made.

We claim:

1. A compact peripheral x-ray densitometer for in vivo bone comprising:

(a) a first positioner to position a human heel with respect to the first positioner (b) a second positioner to position a human forearm with respect to the second positioner;

(c) a housing having receiving means for selectively receiving one of the first and second positioners in a predetermined position with respect to the housing the housing including a means for positioning and supporting the housing at a first angle for use of the first positioner and a second angle for use of the second positioner;

(d) a dual energy radiation source located within the housing aligned with said receiving means for directing radiant energy through bone as received by a positioner;

(e) a detector located within the housing aligned with said receiving means to receive the radiant energy after passage through the bone as received by the positioner to provide an electrical signal dependent on the received radiant energy for each of two energies;

(f) an image processing circuit providing a measure of the bone substantially independent of any surrounding soft tissue;

whereby an equalizing water bath that may interfere with the positioners is eliminated.

2. The compact x-ray densitometer of claim 1 including a third positioner providing a support for a small laboratory animal.

3. Compact peripheral x-ray densitometer of claim 1 wherein the means for positioning and supporting the housing includes:

a first base portion of the housing positioned to support the housing at a first orientation;

a second base portion of the housing positioned to support the housing at a second orientation;

whereby the housing may be rotated to and supported at either of the first and second orientation changing the direction of the x-ray axis.

4. The compact x-ray densitometer of claim 3 wherein the first and second base portions are perpendicular surfaces of the housing.

5. The compact x-ray densitometer of claim 4 wherein the first base portion includes feet to abut a horizontal surface and wherein the second base portion includes fasteners for engaging a vertical wall.

6. The compact x-ray densitometer of claim 1 wherein the radiation source is an x-ray radiation source.

7. The compact x-ray densitometer of claim 1 wherein the radiation source is a radioisotope.

8. The compact x-ray densitometer of claim 1 wherein the first positioner includes an extension providing support to a patient's calf.

9. The compact x-ray densitometer of claim 1 wherein the second positioner includes an outwardly extending surface providing support to a patient's palm.

* * * * *